(12) United States Patent
Wu et al.

(10) Patent No.: US 7,485,621 B2
(45) Date of Patent: Feb. 3, 2009

(54) TUMOR TAG AND THE USE THEREOF

(75) Inventors: Jun Wu, Shanghai (CN); Ying Luo, Shanghai (CN)

(73) Assignee: Shanghai Genomics, Inc., Shanghai (CN)

( * ) Notice: Subject to any disclaimer, the term of this patent is extended or adjusted under 35 U.S.C. 154(b) by 302 days.

(21) Appl. No.: 10/527,257

(22) PCT Filed: Sep. 9, 2002

(86) PCT No.: PCT/CN02/00631

§ 371 (c)(1), (2), (4) Date: Mar. 9, 2005

(87) PCT Pub. No.: WO2004/022589

PCT Pub. Date: Mar. 18, 2004

(65) Prior Publication Data

US 2007/0275419 A1    Nov. 29, 2007

(51) Int. Cl.
| | |
|---|---|
| A61K 38/00 | (2006.01) |
| C12N 15/00 | (2006.01) |
| C12N 5/02 | (2006.01) |
| C12P 21/06 | (2006.01) |
| C12P 21/08 | (2006.01) |
| C07K 1/00 | (2006.01) |
| C07H 21/04 | (2006.01) |
| G01N 33/574 | (2006.01) |

(52) U.S. Cl. ...................... 514/12; 435/320.1; 435/325; 435/69.1; 530/350; 530/388.8; 536/23.5

(58) Field of Classification Search .................... 514/12; 435/320.1, 325, 69.1; 530/350, 388.8; 536/23.5
See application file for complete search history.

(56) References Cited

U.S. PATENT DOCUMENTS

2006/0134663 A1 * 6/2006 Harkin et al. .................. 435/6

FOREIGN PATENT DOCUMENTS

WO    WO 98/19167    5/1998

OTHER PUBLICATIONS

Strausberg et al. (PNAS 99:16899-16903 (Dec. 2002)).*
Protein sequence search alignments for SEQ Id No. 2 and amino acid residues 29-213 of SEQ Id No. 2 (pp. 1-2).*
Sequence search alignment (pp. 1-3) Strausberg et al. (PNAS 99:16899-16903 (Dec. 2002).*
Sequence search alignment (pp. 1-4) Bacon et al. (J. Immunol. 173:1078-1084 (2004).*
McBride et al. (Clin. Chem 35(11):2196-2201 (1989).*
Sequence alignment for SEQ Id No. 1 and SEQ Id No. 2 (Hood et al., U.S. Appl. No. 60/836,968, (filed Aug. 9, 2006)).*
Sequence search for SEQ Id No. 1 (Trowsdale et al., U.S. Appl. No. 10/589,851, (filed Feb. 17, 2005)).*
Sequence search for SEQ Id No. 1 (Harkin et al., U.S. Appl. No. 11/266,748, (filed Nov. 3, 2005)).*
David Cosman et al., *ULBPs, Novel MHC Class I-Related Molecules, Bind to CMV Glycoprotein UL16 and Stimulate NK Cytotoxity through the NKG2D Receptor*, Immunity, vol. 14, pp. 123-133, Feb. 2001.
Mirjana Radosavljevic et al., *A Cluster of Ten Novel MHC Class I Related Genes on Human Chromosome 6q24.2-q25.3*, Genomics, vol. 79, No. 1, Jan. 2002, pp. 114-123.
*Homo sapiens, UL16 binding protein 2, clone MGC:21383 Image: 4747126, mRNA complete cds.*, Aug. 16, 2002, BC034689, 1368 bp, mRNA linear.

* cited by examiner

*Primary Examiner*—David J. Blanchard
*Assistant Examiner*—Lynn Bristol
(74) *Attorney, Agent, or Firm*—Wilson Sonsini Goodrich & Rosati

(57) ABSTRACT

The invention provides a new tumor tag, RL5 protein, the polynucleotide encoding RL5 protein, and the method of producing RL5 protein by recombinant technology. The invention also discloses the use of RL5 protein and the polynucleotides encoding RL5 protein, e.g., in diagnosing and treating tumor, as well as the pharmaceutical composition containing RL5 protein or the antibody against it.

10 Claims, 6 Drawing Sheets

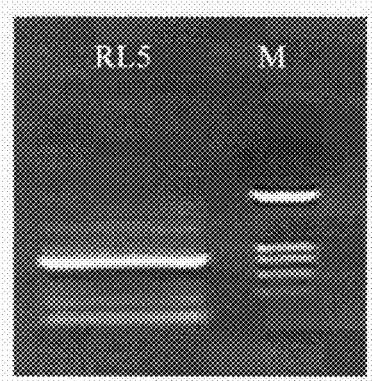

Fig. 1

```
                        10         20         30         40         50         60
SEQ ID NO: 18  ulbp2   MAAAAATKIL LQLPLLLLLS GWSRAGRAIP HSLCYDITVI PKFRPGPRWC AVQGQVDEKT
                       :::::  ::: :::::::::: :: ::: ::: :::::::::: :::::::::: ::::::::::
SEQ ID NO: 2   r15     MAAAASPAFL LRLPLLLLLS SWCRTGLAIP HSLCYDITVI PKFRPGPRWC AVQGQVDEKT
                        10         20         30         40         50         60

70         80         90        100        110        120
               ulbp2   FLHYDCGNKT VTPVSPLGKK LNVTTAWKAG NPVLREVVDI LTEQLRDIQL ENYTPKEPLT
                       :::::::::: :::::::::: :::::::::: :::::::::: :::: :::: ::: ::::::
               r15     FLHYDCGSKT VTPVSPLGKK LNVTTAWKAG NPVLREVVDI LTEQLLDIQL ENYIPKEPLT
                        70         80         90        100        110        120

130        140        150        160        170        180
               ulbp2   LQARMSCEQK AEGHSSGSWQ FSFDGQIFLL FDSEKRMWTT VHPGARKMKE KWENDKVVAM
                       :::::::::: :::::::::: ::::::::::  ::: :::: :::::::::: ::::: :::
               r15     LQARMSCEGK AEGHSSGSWQ LSFDGQIFLL FDSENRMWTT VHPGARKMKE KWENDKDWTW
                       130        140        150        160        170        180

190        200        210        220        230        240
               ulbp2   SFHYFSMGDC TGWLEDFLMG MDSTLEPSAG APLAMSSGTT QLRATATTLI LCCLLIILPC
                       :::::::::: :::::::::: ::::::::::            ::
               r15     SFHYISMGDC TGWLEDFLMG MDSTLEPSAG ———————GTV
                       190        200        210        220        230 ulbp2   FILPGI r15
```

Fig. 2A

| SEQ ID NO: 11 | Ulbp2: | 1 | atggcagcagccgccgctaccaagatccttctgtgcctcccgcttctgctcctgctgtcc | 60 |
| SEQ ID NO: 12 | rl5: | 1 | atggcagcggccgccagccccgcgttccttctacgcctcccgcttctgctcctgctgtcc | 60 |

```
ulbp2:  61 ggctggtcccgggctgggcgagccgaccctcactctctttgctatgacatcaccgtcatc 120
            ||||||  |  ||  ||||  ||||||||||||||||||||||||||||||||||||||
rl5:    61 agctggtgcaggaccgggctggccgaccctcactctctttgctatgacatcaccgtcatc 120 ulbp2: 121 cctaagttcagacctggaccacggtggtgtgcggttcaaggccaggtggatgaaaagact 180
           ||||||||||||||||||||||||||||||||||||||||||||||||||||||||||||
RL5:   121 cctaagttcagacctggaccacggtggtgtgcggttcaaggccaggtggatgaaaagact 180

Ulbp2: 181 tttcttcactatgactgtggcaacaagacagtcacacctgtcagtcccctggggaagaaa 240
           |||||||||||||||||||||||| ||||||||||| |||||||||||||||||||||||
RL5:   181 tttcttcactatgactgtggcagcaagacagtcacacccgtcagtcccctggggaagaaa 240

Ulbp2: 241 ctaaatgtcacaacggcctggaaagcacagaacccagtactgagagaggtggtggacata 300
           ||||||||||||||||||||||||||||||||||||||||||||||||||||||||||||
RL5:   241 ctaaatgtcacaacggcctggaaagcacagaacccagtactgagagaggtggtggacata 300

Ulbp2: 301 cttacagagcaactgcgtgacattcagctggagaattacacacccaaggaaccctcacc 360
           |||||||||||||||| ||||||||||||||||||||| ||||||||||||||||||||
RL5:   301 cttacagagcaactgcttgacattcagctggagaattacatacccaaggaaccctcacc 360

Ulbp2: 361 ctgcaggcaaggatgtcttgtgagcagaaagctgaaggacacagcagtggatcttggcag 420
           ||||||| |||||||||||||||||||||||| |||||||||||| ||||||||||||||
RL5:   361 ctgcaggccaggatgtcttgtgagcagaaagccgaaggacacggcagtggatcttggcag 420

Ulbp2: 421 ttcagtttcgatgggcagatcttcctcctctttgactcagagaagagaatgtggacaacg 480
           |||||||||| |||||||||||||||||||||||||||||||  || |||||||||||||
RL5:   421 ctcagtttcgatggacagatcttcctcctctttgactcagaaaacagaatgtggacaacg 480

Ulbp2: 481 gttcatcctggagccagaaagatgaaagaaaagtgggagaatgacaaggttgtggccatg 540
           |||||||||||||||||||||||||||||||||||||||||||||||||| | || ||||
RL5:   481 gttcatcctggagccagaaagatgaaagaaaagtgggagaatgacaaggatatgaccatg 540

Ulbp2: 541 tccttccattacttctcaatgggagactgtataggatggcttgaggacttcttgatgggc 600
           |||||||||| ||||||||||||||||||| |||||||||||||||||||||||||||||
RL5:   541 tccttccattacatctcaatgggagactgcacaggatggcttgaggacttcttgatgggc 600

Ulbp2: 601 atggacagcaccctggagccaagtgcaggagcaccactcgccatgtcctcaggcacaacc 660
           |||||||||||||||||||||||||||||||    || ||
RL5:   601 atggacagcaccctggagccaagtgcaggaggcacagtctga------------------

Ulbp2: 661 caactcagggccacagccaccaccctcatcctttgctgcctcctcatcatcctcccctgc 720
RL5:       ------------------------------------------------------------

Ulbp2: 721 ttcatcctccctggcatctga
RL5:       ---------------------
```

Fig. 2B

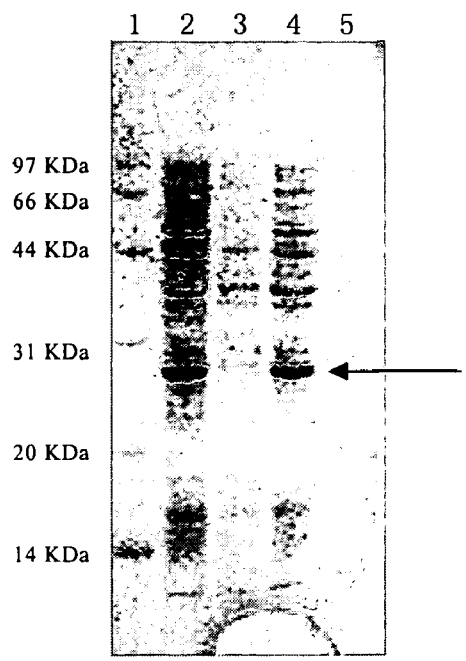
Fig. 5
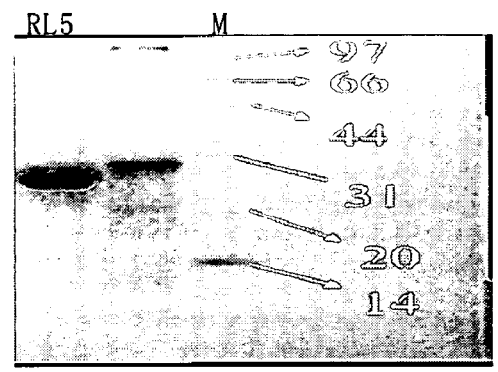
Fig. 6
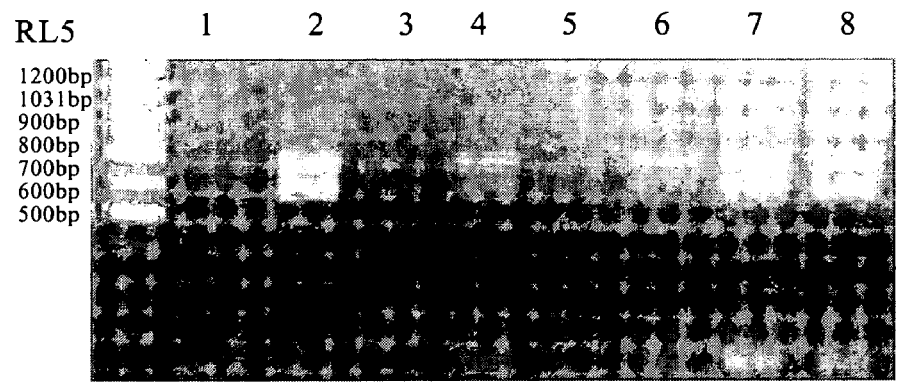
1=stomach; 2=stomach cancer; 3=colon; 4=colon cancer
5=breast; 6=breast cancer; 7=kidney; 8=kidney cancer
Fig. 7

TUMOR TAG AND THE USE THEREOF

CROSS-REFERENCE TO RELATED APPLICATION

This Application is a Section 371 National Stage Application of International Application No. PCT/CN2002/000631, filed 09 Sep. 2002 and published as WO 2004/022589 A1 on 18 Mar. 2004, the subject matter of which is hereby incorporated by reference in its entirety.

FIELD OF INVENTION

This invention relates to the field of biotechnology and medicine. In particular, it relates to a novel tumor tag of RL5 protein, the polynucleotide encoding RL5 protein, and the method of producing RL5 protein by recombinant technology. The invention also discloses the use of RL5 protein and the polynucleotides encoding RL5 protein, e.g., in diagnosing and treating tumor, as well as the pharmaceutical composition containing RL5 protein or the antibody against it.

TECHNICAL BACKGROUND

Since the 1950's, cancer diagnosis and treatment have made significant progress, particularly in the areas of identification of tumor-specific oncogenes and tumor suppressor genes.

Forty years ago, Lewis Thomas and Macfarlane Burnet proposed an immune surveillance mechanism against malignant cells. Recent studies on natural killer cells and T cells have not only provided new evidences supporting such hypothesis, but also uncovered a potential molecular mechanism underlining the immune surveillance process.

Natural killer cells (NK cells) are critical players involved in the first line of defense against pathogens and other detrimental signals. NK cells are capable of recognizing target cells and subsequently eliminating these cells through secretion of cytotoxic mediators. Since NK cells' function does not depend upon antigen/mitogen stimulation, nor does it require mediation through antibody or complement, these cells therefore should possess a recognition system to distinguish between normal and unhealthy targets. The current view is the NK cell function is regulated through a balance between its surface activating and inhibitory receptors. Major histocompatibility complex (MHC) class-1 molecules on the surface of all cells are recognized by NK cell receptors, including murine Ly49 (recognizing H-2K and H-2D) and human killer inhibitory receptors (KIR) (recognizing HLA-A, -B, -C), resulting in inhibiting NK cell's function. In viral-infected or tumor cells, these MHC class-1 molecules are frequently down regulated. A reduction of the engagement of the inhibitory receptors on NK cells causes the activation of NK cells, thereby killing these abnormal cells.

In addition to NK cells, T cells are also involved in preventing skin cancer formation induced by certain carcinogens. In human and mice, γδ-T cells in skin and gut epithelium are known to participate in local immunity. It has been shown that these T cells are involved in immune surveillance against transformation of gut epithelial cells. Moreover, recent studies have also demonstrated that these T cells are important players in eliminating transformed cells induced by exogenous carcinogen. The induction of two MHC class-I related molecules, MIC-A and MIC-B, on abnormal cells has been shown to be involved in the immune surveillance processes.

Bauer et al (Bauer S, et al., Science 1999 Jul 30; 285(5428): 727-9) have identified NKG2D as a receptor for MIC-A and MIC-B through representational differential analysis (RDA), which is a orphan C-type lectin-like NK cell receptor with unknown expression and function.

Several NK cell receptors, which are specific to MHC-1 or the MHC-1-related molecules, have been found. Unlike other NK cell receptors, NKG2D is an activating receptor present on all NK cells, γδ-T cells, and some CD8+ T cells. It forms a receptor complex with a transmembrane signaling adaptor, DAP10, in which its cytoplasmic domain contains a YxxM sequence motif capable of activating PI3 kinase-mediated signaling pathways (Wu J, et al., Science 1999 Jul. 30; 285 (5428): 730-2).

There is no MICA or MICB homologue in mice. However, it was subsequently found in mice that a family of glycoproteins called RAE-1 also served as ligands for murine NKG2D (Cerwenka A, et al., Immunity 2000 June; 12 (6): 721-7). Recent studies have revealed that there are at least five RAE-1 molecules (RAE-1-α, -β, -γ, -δ, -ε) and one RAE-1-related molecule H60. These molecules are absent or low expressed in normal tissues but are highly expressed in certain malignant tissues or upon treatment with retinoic acid. Their expression can also be found in tumors induced by carcinogen TPA. Recent studies by Diefenbach et al. (Nature 2001 Sep. 13; 413(6852): 165-71) and Cerwenka et al. (Proc Natl Acad Sci USA 2001 Sep. 25; 98 (20): 11521-6) have demonstrated that transfection of RAE-1 in MHC class-I expressing tumor cells results in rejection of these tumors by NK cells in mice. Similar to NK cells, murine γδ-T cells can also kill inoculated squamous carcinoma cell line in vivo via NKG2D, and under certain experimental conditions, RAE-1 can induce γδ-T cell memory response against transplanted tumors.

The subsequent studies have uncovered RAE-1 homologues in human, including ULBP-1, ULBP-2, and ULBP-3. These molecules were initially identified as interacting partners with human cytomegaloviral glycoprotein UL16. Although ULBP molecules are related to MHC class-1, they are not close to MICB, which is also capable to bind UL16. ULBP is also the ligand for NKG2D and is capable to stimulate NK cell to express cytokine and chemokine. The expression of ULBP in target cells against NK cells prevent them from attacking by NK cells. In the cytomegalovirus infection, the ULBP or MIC antigen may be veiled by UL16 protein so as to avoid the attacks from the immune system.

Taken together, numerous studies in human and mice indicate NKG2D plays a vital role in immune responses mediated by NK cells, γδ-TCR+T cells, CD8+αβ-TCR+T cells against virus and tumors.

Since the 1990's, research in tumor immunology has made some breakthroughs. Immune treatment of cancer comes to a new era. Many immune treatments have been in clinical level, mainly by activating the immune cells of patients in vivo or in vitro to recognize malignant cells. The further proliferation of such immune cells eliminates or inhibits the growth of malignant cells. In 1991, human tumor rejection antigen was discovered for the first time. From then on, numerous studies indicate that most of the tumor cells have different molecules from normal cells, which could be recognized and attacked by immune system. Such molecules are called tumor rejection antigen. Human immune cells capable of tumor killing can be induced in vivo and in vitro by tumor rejection antigen. Therefore, tumor rejection antigens are the most important component in tumor immune treatment.

So far, several tumor antigens have been discovered in melanoma and other tumor tissues including prostate tumor, thymus tumor, ovarian tumor and gastrointestinal tumor.

Tumor rejection antigens discovered by now are classified into four types. The first type is from somatic mutations of normal genes and the second is from the mutation of genes related to tumor progressing. These two types have patient specificity, which are not available for generalized treatment. The third type of antigen expresses in normal tissues but their expression levels are highly elevated in tumors. If their genes are not mutated, these antigens are universal in tumor patients. However, they have strict tissue specificity rather than tumor specificity so that they do not have significance in clinical treatment. The fourth type has strict tumor specificity and is related to tumor progression. Because they are widely expressed in humor tumor, these tumor antigens are suitable candidates to be tumor markers and targets of anti-tumor immune response. However, very few antigens discovered by now belong to the fourth type.

Therefore, there is a keen need in the art to develop new tumor rejection antigen of the fourth type, which can be used as a tumor tag for tumor diagnosis and treatment.

SUMMARY OF INVENTION

One purpose of the invention is to provide a novel human tumor tag, which was named RL5 protein, and its fragments, analogs and derivatives.

Another purpose of the invention is to provide a polynucleotide encoding said polypeptides.

Still another purpose of the invention is to provide a method for preparing said polypeptides and the use of said polypeptides and their encoding sequences. After comprehensive and intensive researches, the inventors have found and isolated a novel antigen gene, RL5, which is useful as a tumor tag. RL5 gene is not expressed or low expressed in normal tissues, but is widely expressed in tumor tissues. The expression product of RL5 is a secretory protein. RL5 binds to NKG2D receptors with high efficiency. On the basis of said discovery, the inventors completed this invention.

In the 1st aspect, the invention provides an isolated RL5 polypeptide, which comprises a polypeptide having the amino acid sequence of SEQ ID NO: 2, its conservative variants, its active fragments, and its active derivatives. Preferably, the polypeptide is selected from the group consisting of: (a) a polypeptide consisting of the amino acid sequence of 1-213 of SEQ ID NO: 2 or the amino acid sequence of 29-213 of SEQ ID NO: 2; (b) a polypeptide having the function of binding to NKG2D and derived from the polypeptide of (a) by substituting, deleting or adding one or more amino acid residues in the amino acid sequence of 1-213 of SEQ ID NO: 2 or the amino acid sequence of 29-213 of SEQ ID NO: 2

In the 2nd aspect, it provides an isolated polynucleotide comprising a nucleotide sequence sharing at least 70% identity to the following nucleotide sequences: (a) a polynucleotide encoding the RL5 polypeptide; (b) the polynucleotide complementary to polynucleotide of (a). Preferably, said polynucleotide encodes a polypeptide comprising the amino acid sequence of the amino acid sequence of 1-213 of SEQ ID NO: 2 or the amino acid sequence of 29-213 of SEQ ID NO: 2. More preferably, said polynucleotide is selected from the group consisting of (a) the nucleotide sequence of 85-639 of SEQ ID NO: 1; (b) the nucleotide sequence of 1-639 of SEQ ID NO: 1; and (c) the nucleotide sequence of 1-720 of SEQ ID NO: 1.

In the 3rd aspect, it provides a vector comprising the above polynucleotide, and a host cell transformed with the vector or polynucleotide.

In the 4th aspect, it provides a method for producing RL5 protein, which comprises:
(a) culturing the above transformed host cell under the expression conditions;
(b) isolating RL5 protein from the culture.

In the 5th aspect, it provides an antibody specifically binding RL5 protein. Also provided are nucleic acid molecules comprising consecutive 15-720 nucleotides of the above polynucleotide.

In the 6th aspect, it provides compounds that simulate, promote and antagonize RL5 activity, or inhibit RL5 expression and methods for screening and preparing these compounds. Preferably, the compounds are antisense sequences of RL5 encoding sequence or fragments thereof.

In the 7th aspect, it provides a method for detecting the presence of RL5 protein in a sample comprising: contacting the sample with an antibody specifically against RL5 protein, and observing the formation of antibody complex which indicates the presence of RL5 protein in the sample. It also provides a method for detecting tumor, comprising the step of detecting the presence of RL5 in the sample of the subject, such as blood, urine, body fluid, and saliva.

In the 8th aspect, it provides a kit for detecting tumor comprising a pair of primers specifically amplifying RL5 and/or an antibody specifically against RL5 protein. The kit may further contain the specific probes and/or PCR buffers and so on.

In the 9th aspect, it provides the uses of RL5 and its encoding sequence, e.g., in screening RL5 agonists and antagonist, and peptide fingerprinting. The RL5 encoding sequence and its fragments can be used as primers in PCR, or probes in hybridization and microarray.

In the 10th aspect, it provides a pharmaceutical composition comprising a safe and efficient amount of RL5 antagonist and a pharmaceutically acceptable carrier. The preferred RL5 antagonists are antibodies against RL5 protein or antisense nucleotide sequence of RL5 gene. The pharmaceutical composition can be used to treat tumors or enhance immunity.

The other aspects of invention will be apparent to artisan in light of the teaching of the invention.

DESCRIPTION OF DRAWINGS

FIG. 1 shows the electrophoresis of RL5 gene.

FIG. 2A shows the alignment of amino-acid sequence ULBP-2 (SEQ ID NO: 10) and RL5 (SEQ ID NO: 2). The shadowed area indicates the signal peptide, and the underlined area indicates the transmembrane region of ULBP-2.

FIG. 2B shows the alignment of nucleotide sequence of ULBP-2 (SEO ID NO: 11) and RL5 (SEQ ID NO: 12).

FIG. 5 shows the induced expression of RL5 in $E.$ $coli$ DH5α cells. Lane 1 indicates the protein marker (97, 66, 44, 31, 20, 14 kDa, respectively), Lanes 2 and 4 indicate the samples after induction, while Lanes 3 and 5 indicate the samples before induction. The arrow shows the band position of RL5.

FIG. 6 shows the electrophoresis of purified RL5 protein.

FIG. 7 show the mRNA expression spectrums of RL5 in various tumor samples.

DETAILED DESCRIPTION

Figure 3A:
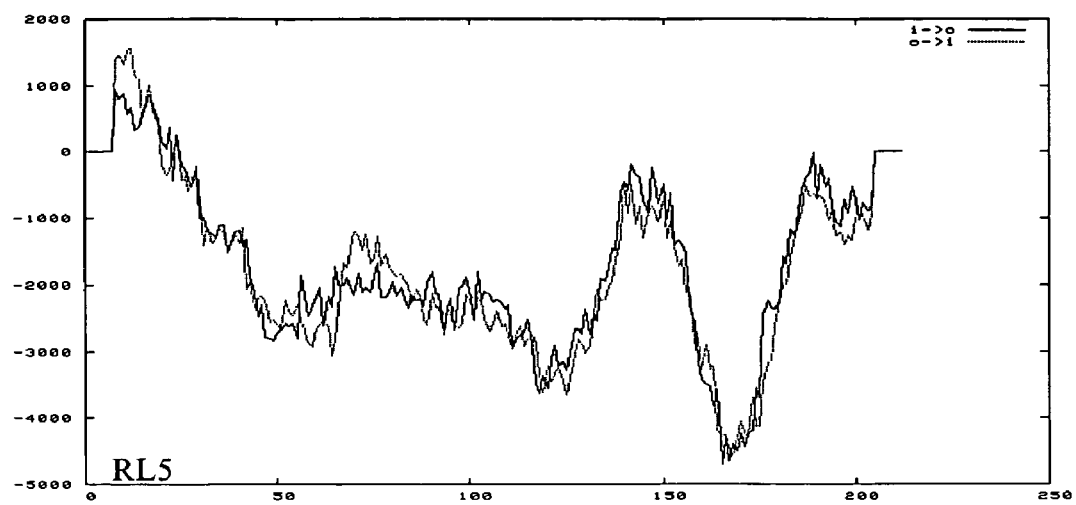
FIGS. 3A and 3B show hydrophobicity profiles of RL5 and ULBP-2 in the analysis of their transmembrane regions, respectively.

As used herein, the term "RL5 protein", "RL5 polypeptide" or "tumor tag RL5" are exchangeable, referring to a protein or polypeptide comprising or consisting of the amino acid sequence of tumor tag RL5 (SEQ ID NO: 2). The term also includes the mature RL5 without the signal peptide, i.e., 1-28 of SEQ ID NO: 2.

As used herein, the term "isolated" refers to a substance which has been isolated from the original environment. For naturally occurring substance, the original environment is the natural environment. E.g., the polynucleotide and polypeptide in a naturally occurring state in the viable cells are not isolated or purified. However, if the same polynucleotide and polypeptide have been isolated from other components naturally accompanying them, they are isolated or purified.

As used herein, the terms "isolated RL5 protein or polypeptide" mean that RL5 polypeptide does not essentially contain other proteins, lipids, carbohydrate or any other substances associated therewith in nature. The artisans can purify RL5 protein by standard protein purification techniques. Essentially purified polypeptide forms a single main band on a non-reductive PAGE gel.

The polypeptide of invention may be a recombinant polypeptide, natural polypeptide, or synthetic polypeptide, preferably a recombinant polypeptide. The polypeptide of invention may be a purified natural product or a chemically synthetic product. Alternatively, it may be produced from prokaryotic or eukaryotic hosts, such as bacteria, yeast, higher plant, insect, and mammalian cells, using recombinant techniques. According to the host used in the protocol of recombinant production, the polypeptide of invention may be glycosylated or non-glycosylated. The polypeptide of invention may or may not comprise the starting Met residue.

The invention further comprises the fragments, derivatives and analogues of RL5. As used in the invention, the terms "fragment", "derivative" and "analogue" mean the polypeptide that essentially retains the same biological functions or activity of RL5 protein of the invention. The fragment, derivative or analogue of the polypeptide of invention may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues include a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretary sequence or a sequence which is employed for purification of the mature polypeptide or a proprotein sequence, e.g., a fusion protein formed with IgC fragment. Such fragments, derivatives and analogs are deemed to be within the scope of those skilled in the art from the teachings herein.

In the present invention, the term "human RL5 polypeptide" refers to a full-length polypeptide having the activity of human RL5 protein comprising the amino acid sequence of SEQ ID NO: 2, or the mature polypeptide thereof. The term also comprises the variants of said amino acid sequence which have the same function of human RL5. These variants include, but are not limited to, deletions, insertions and/or substitutions of several amino acids (typically 1-50, preferably 1-30, more preferably 1-20, most preferably 1-10), and addition of one or more amino acids (typically less than 20, preferably less than 10, more preferably less than 5) at C-terminal and/or N-terminal. For example, the protein functions are usually unchanged when an amino residue is substituted by a similar or analogous one. Further, the addition of one or several amino acids at C-terminal and/or N-terminal will not change the function of protein. The term also includes the active fragments and derivatives of RL5 protein.

The variants of polypeptide include homologous sequences, allelic variants, natural mutants, induced mutants, proteins encoded by DNA which hybridizes to RL5 DNA under high or low stringency conditions as well as the polypeptides or proteins retrieved by antisera raised against RL5 polypeptide. The present invention also provides other polypeptides, e.g., fusion proteins, which include the RL5 polypeptide or fragments thereof. In addition to substantially full-length polypeptide, the soluble fragments of RL5 polypeptide are also included. Generally, these fragments comprise at least 10, typically at least 30, preferably at least 50, more preferably at least 80, most preferably at least 100 consecutive amino acids of RL5 polypeptide.

The present invention also provides the analogues of RL5 protein or polypeptide. Analogues can differ from naturally occurring RL5 polypeptide by amino acid sequence differences or by modifications that do not affect the sequence, or by both. These polypeptides include genetic variants, both natural and induced. Induced variants can be made by various techniques, e.g., by random mutagenesis using irradiation or exposure to mutagens, or by site-directed mutagenesis or other known molecular biologic techniques. Also included are analogues which include residues other than those naturally occurring L-amino acids (e.g., D-amino acids) or non-naturally occurring or synthetic amino acids (e.g., beta- or gamma-amino acids). It is understood that the polypeptides of the invention are not limited to the representative polypeptides listed hereinabove.

Modifications (which do not normally alter primary sequence) include in vivo or in vitro chemical derivation of polypeptides, e.g., acetylation, or carboxylation. Also included are modifications of glycosylation, e.g., those made by modifying the glycosylation patterns of a polypeptide during its synthesis and processing or in the further processing steps, e.g., by exposing the polypeptide to enzymes which affect glycosylation (e.g., mammalian glycosylating or deglycosylating enzymes). Also included are sequences that have phosphorylated amino acid residues, e.g., phosphotyrosine, phosphoserine, phosphothreonine, as well as sequences that have been modified to improve their resistance to proteolytic degradation or to optimize solubility properties.

In the invention, "RL5 conservative mutant" means a polypeptide formed by substituting at most 10, preferably at most 8, more preferably 5, and most preferably at most 3 amino acids with the amino acids having substantially the same or similar property, as compared with the amino acid sequence of SEQ ID NO: 2. Preferably, these conservative mutants are formed by the substitution according to Table 1.

TABLE 1

| Initial residue | Representative substitution | Preferred substitution |
|---|---|---|
| Ala (A) | Val; Leu; Ile | Val |
| Arg (R) | Lys; Gln; Asn | Lys |

TABLE 1-continued

| Initial residue | Representative substitution | Preferred substitution |
|---|---|---|
| Asn (N) | Gln; His; Lys; Arg | Gln |
| Asp (D) | Glu | Glu |
| Cys (C) | Ser | Ser |
| Gln (Q) | Asn | Asn |
| Glu (E) | Asp | Asp |
| Gly (G) | Pro; Ala | Ala |
| His (H) | Asn; Gln; Lys; Arg | Arg |
| Ile (I) | Leu; Val; Met; Ala; Phe | Leu |
| Leu (L) | Ile; Val; Met; Ala; Phe | Ile |
| Lys (K) | Arg; Gln; Asn | Arg |
| Met (M) | Leu; Phe; Ile | Leu |
| Phe (F) | Leu; Val; Ile; Ala; Tyr | Leu |
| Pro (P) | Ala | Ala |
| Ser (S) | Thr | Thr |
| Thr (T) | Ser | Ser |
| Trp (W) | Tyr; Phe | Tyr |
| Tyr (Y) | Trp; Phe; Thr; Ser | Phe |
| Val (V) | Ile; Leu; Met; Phe; Ala | Leu |

The polynucleotide according to the invention may be in the forms of DNA and RNA. DNA includes cDNA, genomic DNA, and synthetic DNA, etc., in single strand or double strand form. A single strand DNA may be an encoding strand or non-encoding strand. The coding sequence for mature polypeptide may be identical to the coding sequence shown in SEQ ID NO: 1, or may be a degenerate sequence. As used herein, the term "degenerate sequence" means an sequence which encodes a protein or peptide comprising a sequence of SEQ ID NO: 2 and which has a nucleotide sequence different from the sequence of coding region in SEQ ID NO: 1.

The sequences encoding the mature RL5 polypeptide of SEQ ID NO: 2 include those encoding only the mature polypeptide, those encoding mature polypeptide plus various additional encoding sequence, the encoding sequence for mature polypeptide plus the non-encoding sequence and optional additional encoding sequence. The term "polynucleotide encoding the polypeptide" includes the polynucleotide encoding said polypeptide and the polynucleotide comprising additional and/or non-encoding sequence.

The invention further relates to the variants of the hereinabove polynucleotides which encode a polypeptide having the same amino acid sequence of invention, or its fragment, analogue and derivative. The variant of the polynucleotide may be a naturally occurring allelic variant of the polynucleotide or a non-naturally occurring variant of the polynucleotide. Such nucleotide variants include substitution, deletion, and insertion variants. As known in the art, the allelic variant is a substitution form of polynucleotide, which may be a substitution, deletion, and insertion of one or more nucleotides without substantially changing the functions of the encoded polypeptide.

The present invention further relates to polynucleotides, which hybridize to the hereinabove-described sequences, if there is at least 50%, preferably at least 70%, more preferably at least 80%, and most preferably at least 90% or 95% identity between the sequences. The present invention particularly relates to polynucleotides, which hybridize under stringent conditions to the polynucleotides of the invention. As herein used, the term "stringent conditions" means the following conditions: (1) hybridization and washing under low ionic strength and high temperature, such as 0.2×SSC, 0.1% SDS, 60° C.; (2) hybridization after adding denaturants, such as 50% (v/v) formamide, 0.1% bovine serum/0.1% Ficoll, 42° C.; or (3) hybridization of two sequences sharing at least 90%, preferably 95% homology. Further, the polynucleotides which hybridize to the hereinabove described polynucleotides encode a polypeptide which retains the same biological function or activity as the mature polypeptide shown in SEQ ID NO: 2.

The invention also relates to nucleic acid fragments hybridized with the hereinabove sequence. As used in the present invention, the length of the "nucleic acid fragment" is at least 15 bp, preferably at least 30 bp, more preferably at least 50 bp, and most preferably at least 100 bp. The nucleic acid fragment can be used in the amplification techniques of nucleic acid, e.g., PCR, so as to determine and/or isolate the polynucleotide encoding RL5 protein.

The full-length RL5 nucleotide sequence or its fragment can be prepared by PCR amplification, recombinant method and synthetic method. For PCR amplification, one can obtain said sequences by designing primers based on the nucleotide sequence disclosed herein, especially the ORF, and using cDNA library commercially available or prepared by routine techniques in the art as a template. When the sequence is long, it is usually necessary to perform two or more PCR amplifications and link the amplified fragments together correctly.

Once the sequence is obtained, one can produce lots of the sequences by recombinant methods. Usually, said sequence is cloned into a vector which is then transformed into a host cell. The sequence is isolated from the amplified host cells using conventional techniques.

Further, the sequence can be synthesized, especially when the fragment is short. Typically, several small fragments are synthesized and linked together to obtain a long sequence.

It is completely feasible to chemically synthesize the DNA sequence encoding the protein of invention, or the fragments or derivatives thereof. Then, the DNA sequence can be introduced into the various DNA molecules (such as vectors) and cells available in the art. In addition, the mutation can be introduced into the protein sequence by chemical synthesis.

The method of amplification of DNA/RNA by PCR is preferably used to obtain the gene of the invention. The primers used in PCR can be properly selected according to the polynucleotide sequence information of invention disclosed herein and synthesized by the conventional methods. The amplified DNA/RNA fragments can be isolated and purified by conventional methods such as gel electrophoresis.

The invention further relates to a vector comprising the polynucleotide of the invention, a genetic engineered host cell transformed with the vector of the invention or directly with the sequence encoding RL5 protein, and the method for producing the polypeptide of invention by recombinant techniques.

The recombinant human RL5 polypeptides can be expressed or produced by the conventional recombinant DNA technology, using the polynucleotide sequence of invention. Generally, it comprises the following steps:

(1) transfecting or transforming the appropriate host cells with the polynucleotide or its variants encoding RL5 polypeptide of the invention or the vector containing said polynucleotide;

(2) culturing the host cells in an appropriate medium;

(3) isolating or purifying the protein from the medium or cells.

In the present invention, the polynucleotide sequences encoding human tumor tag may be inserted into a recombinant expression vector. On the whole, any plasmid or vector can be used to construct the recombinant expression vector as long as it can replicate and is stable in the host. One important feature of expression vector is that the expression vector typically contains an origin of replication, a promoter, a marker gene as well as the translation regulatory components.

The methods known by the artisans in the art can be used to construct an expression vector containing the DNA sequence of RL5 and appropriate transcription/translation regulatory components. These methods include in vitro recombinant DNA technique, DNA synthesis technique, in vivo recombinant technique and so on. The DNA sequence is efficiently linked to the proper promoter in an expression vector to direct the synthesis of mRNA. The expression vector may further comprise a ribosome-binding site for initiating the translation, transcription terminator and the like.

Further, the expression vector preferably comprises one or more selective marker genes to provide a phenotype for the selection of the transformed host cells, e.g., the dehydrofolate reductase, neomycin resistance gene and GFP (green flurencent protein) for eukaryotic cells, as well as tetracycline or ampicillin resistance gene for E. coli.

The vector containing said DNA sequence and proper promoter or regulatory elements can be transformed into appropriate host cells to express the protein.

The "host cell" includes prokaryote, such as bacteria; primary eukaryote, such as yeast; advanced eukaryotic, such as mammalian cells. The representative examples are bacterial cells, such as E. coli, Streptomyces, Salmonella typhimurium; fungal cells, such as yeast; plant cells; insect cells such as Drosophila S2 or Sf9; animal cells such as CHO, COS or 293 cells, etc.

Recombinant transformation of host cell with the DNA sequence of invention might be carried out by conventional techniques well known to those skilled in the art. Where the host is prokaryotic such as E. coli, the competent cells, which are capable of DNA uptake, can be prepared from cells harvested after exponential growth phase and subsequently treated by the $CaCl_2$ method using procedures well known in the art. Alternatively, $MgCl_2$ can be used. The transformation can also be carried out by electroporation, if desired. When the host is an eukaryote, such methods of transfection of DNA as calcium phosphate co-precipitates, conventional mechanical procedures such as micro-injection, electroporation, or liposome-mediated transfection may be used.

The transformants are cultured using conventional methods to express the polypeptides of the invention. According to the used host cells, the medium for cultivation can be selected from various conventional mediums. The host cells are cultured under a condition suitable for its growth until the host cells grow to an appropriate cell density. Then, the selected promoter is induced by appropriate means (e.g., temperature shift or chemical induction) and cells are cultured for an additional period.

In the above methods, the recombinant polypeptide may be included in the cells, or expressed on the cell membrane, or secreted out of the cell. If desired, the physical, chemical and other properties can be utilized in various isolation methods to isolate and purify the recombinant protein. These methods are well-known to those skilled in the art and include, but are not limited to conventional renaturation treatment, treatment by protein precipitant (such as salt precipitation), centrifugation, cell lysis by osmosis, sonication, supercentrifugation, molecular sieve chromatography or gel chromatography, adsorption chromatography, ion exchange chromatography, HPLC, and any other liquid chromatography, and the combination thereof.

Therefore, the recombinant human RL5 protein or polypeptide have various uses including, but not to be limited to: screening out antibodies, polypeptides or other substances which inhibit the function of RL5 protein.

In another aspect, the invention also includes polyclonal and monoclonal antibodies (mAbs), preferably mAbs, which are specific for polypeptides encoded by RL5 DNA or fragments thereof. By "specificity", it means an antibody which binds to the RL5 gene products or a fragments thereof. Preferably, the antibody binds to the RL5 gene products or fragments thereof and does not substantially recognize nor bind to other antigenically unrelated molecules. Antibodies which bind to RL5 and block RL5 protein and those which do not affect the RL5 function are included in the invention.

The invention includes intact monoclonal or polyclonal antibodies, and immunologically-active antibody fragments, e.g., a Fab' or $(Fab)_2$ fragment, an antibody heavy chain, an antibody light chain, or a chimeric antibody.

The antibody against RL5 can be used in immunohistochemical method to detect the presence of RL5 protein in biopsy specimen.

The antibodies of the invention can be used to treat or prevent RL5-related human diseases such as tumor. One common method is to challenge the amino group on the antibody with sulfydryl cross-linking agents, such as SPDP, and bind the toxin onto the antibody by interchanging the disulfide bonds. This hybrid antibody can be used to kill RL5 protein-positive cells such as tumor cells.

The substances that act with RL5 protein, e.g., receptors, inhibitors, agonists and antagonists, can be screened out by various conventional techniques, using RL5 protein of the invention.

The RL5 protein, antibody, inhibitor, agonist or antagonist of the invention provide different effects when administrated in therapy. Usually, these substances are formulated with a non-toxic, inert and pharmaceutically acceptable aqueous carrier. The pH typically is about 5-8, preferably 6-8, although pH may alter according to the property of the formulated substances and the diseases to be treated. The formulated pharmaceutical composition is administrated in conventional routes including, but not limited to, intramuscular, intraperitoneal, intravenous, subcutaneous, intradermal or topical administration.

The RL5 antagonists such as antibody and antisense sequence can be directly used for curing disorders, e.g., tumors, which include, but are not limited to: stomach cancer, colon cancer, breast cancer, lung cancer, liver cancer, prostate cancer and leukemia. The RL5 protein can be administrated in combination with other medicaments, e.g., TNF-α, TNF-β and so on.

The invention also provides a pharmaceutical composition comprising safe and effective amount of RL5 antagonist in combination with a pharmaceutically acceptable carrier. Such a carrier includes but is not limited to saline, buffer solution, glucose, water, glycerin, ethanol, or the combination thereof. The pharmaceutical formulation should be suitable for delivery method. The pharmaceutical composition may be in the form of injections that are made by conventional methods, using physiological saline or other aqueous solution containing glucose or auxiliary substances. The pharmaceutical compositions in the form of tablet or capsule may be prepared by routine methods. The pharmaceutical compositions, e.g., injections, solutions, tablets, and capsules, should be manufactured under sterile conditions. The active ingredient is administrated in therapeutically effective amount, e.g., about 1 ug-10 mg/kg body weight per day.

The invention further provides diagnostic assays for quantitative and in situ measurement of RL5 protein level. These assays are known in the art and include FISH assay and radioimmunoassay. The level of RL5 protein detected in the assay can be used to detect tumor.

A method of detecting RL5 protein in a sample by utilizing the antibody specifically against RL5 protein comprises the steps of: contacting the sample with the antibody specifically against RL5 protein; observing the formation of antibody complex which indicates the presence of RL5 protein in the sample.

The polynucleotide encoding RL5 protein can be used in the diagnosis and treatment of RL5 related diseases. A part of or all of the polynucleotides of the invention can be used as probe and fixed on a microarray or DNA chip for analyzing the differential expression of genes in tissues and for the diagnosis of genes. The RL5 specific primers can be used in RT-PCR and in vitro amplification to detect the transcripts of RL5.

The invention also provides a kit for detecting tumor comprising a pair of primers specifically amplifying RL5 and/or an antibody specifically against RL5 protein. The kit may further contain the specific probes and/or PCR buffers and so on.

The sequencing data of RL5 showed that, RL5 shared certain identity with ULBP-1, ULBP-2, and ULBP-3, with highest identity (about 80%) with ULBP-2. The analysis of expression showed that, RL5 gene was expressed only in tumor tissues, while it was not expressed or low expressed in normal cells. Further, it is of interest that RL5 is a secretory protein which is secreted into the body fluid. Therefore, RL5 is an effective tumor tag useful in the diagnosis and treatment of various cancers.

Since RL5 is possibly a tumor specific rejection antigen which is secreted into body fluid, the direct detection of RL5 in blood sample or urine sample can be used not only as an indication for auxiliary diagnosis and prognosis of tumor, but also as a basis for early diagnosis of tumor.

In addition to diagnosis application, RL5 also has potential use in the tumor surgery. It is helpful to determine the depth and boundary of the tumor invasion and the hidden parts of tumor. In radioimmunoguided surgery (RIGS), a radioisotope labeled antibody against tumor-related antigen is injected into the body for imaging. Base on the analysis of images, the range of tumor invasion can be accurately determined.

In the respect of immunotherapy of tumor, RL5 or fusion protein containing RL5 can be used as immunostimulant, which binds to the NKG2D receptor on the surface of NK cells, γδ-TCR+T cells, CD8+αβ-TCR+T cells to activate these cells so that the cytotoxins are released to kill the tumor cells. Meanwhile, the cells against tumor are amplified in the body to enhance the immunity. In the respect of tumor vaccine, RL5 is useful in preparing molecular tumor vaccine. Tumor vaccine is the main portion of active immunity and is classified into 4 types, i.e., cell tumor vaccine, sub-cell tumor vaccine, molecular tumor vaccine and gene tumor vaccine. The former two types are previous tumor vaccines having very different clinical effects, most of which are not ideal for long-term therapy. The molecular tumor vaccine is based on the interaction between antibody and antigen so that an idiotype antibody against tumor can be prepared. As an idiotype tumor vaccine, it has certain clinical effects. The tumor antigenic peptide can be produced industrially without the risk associated with tumor inoculation and without inhibitory components from tumor cells. When RL5 is used as a tumor antigenic peptide, the resultant molecular vaccine is not limited by the MHC and is applicable to various tumors. In addition to molecular tumor vaccine, another preferred type of tumor vaccine is gene tumor vaccine formed by inserting RL5 gene in series into the viral vector.

Moreover, RL5 is useful to enhance or inhibit immunity. Since RL5 polypeptide and its derivatives can bind to the important stimulating immunological receptor, human NKG2D, and may activate or inhibit the immunity, it is useful in treating autoimmune disease or immunologic rejection, etc.

The invention is further illustrated by the following examples. These examples are only intended to illustrate the invention, but not to limit the scope of the invention. For the experimental methods in the following examples, they are performed under routine conditions, e.g., those described by Sambrook. et al., in Molecule Clone: A Laboratory Manual, New York: Cold Spring Harbor Laboratory Press, 1989, or as instructed by the manufacturers, unless otherwise specified.

EXAMPLE 1

Isolation of the RL5 Gene

When studying the ULBP3 gene, standard PCR was performed using a human Jurkat cell cDNA library conventionally constructed as the template and the following designed primers. Results were shown in FIG. 1.

```
                                          (SEQ ID NO:3)
Forward     5' cggaattcatggcagcggccgccagcccc 3'
primer:

(SEEQ ID NO:4)
Reverse     5' gccaagcttgatgccagggaggatgaagca 3'
primer:
```

As shown in FIG. 1, several bands were obtained by PCR using this pair of primers, and the main band was approximately 700 bp in size. The fragments were isolated, cloned into a vector and sequenced. A 720 bp sequence was obtained (SEQ ID NO: 1). After analysis, it was found that this DNA fragment was not ULBP3, but a novel gene, which was named RL5.

EXAMPLE 2

Sequence Analysis and Mapping of RL5 Gene

The 720 bp DNA fragment obtained in Example 1 (SEQ ID NO: 1) included the whole coding region of RL5 gene. The open reading frame or ORF was from nucleotide 1 to nucleotide 639, encoding a protein of 213 amino acids (SEQ ID NO: 2). Based on the information of EST, the RL5 gene was mapped onto human chromosome 6q25.1.

The results of homology comparison on nucleotide level between RL5 coding region and other family members of ULBP (ULBP1-4) were as followed:

| | Seq | | | | |
|---|---|---|---|---|---|
| | ulbp1 | ulbp2 | ulbp3 | ulbp4 | RL5 |
| ulbp1 | 1.000 | 0.715 | 0.334 | 0.385 | 0.678 |
| ulbp2 | — | 1.000 | 0.311 | 0.387 | 0.811 |
| ulbp3 | — | — | 1.000 | 0.261 | 0.284 |
| ulbp4 | — | — | — | 1.000 | 0.339 |
| RL5 | — | — | — | — | 1.000 |

The results showed that RL5 shared the highest homology with ULBP2 (81%). According to software analysis, nucleotides 1-631 of RL5 shared 94% identity to ULBP2, and RL5 hit a stop codon several amino acids earlier at its 3' end (FIG. 2B).

Figure 3B:
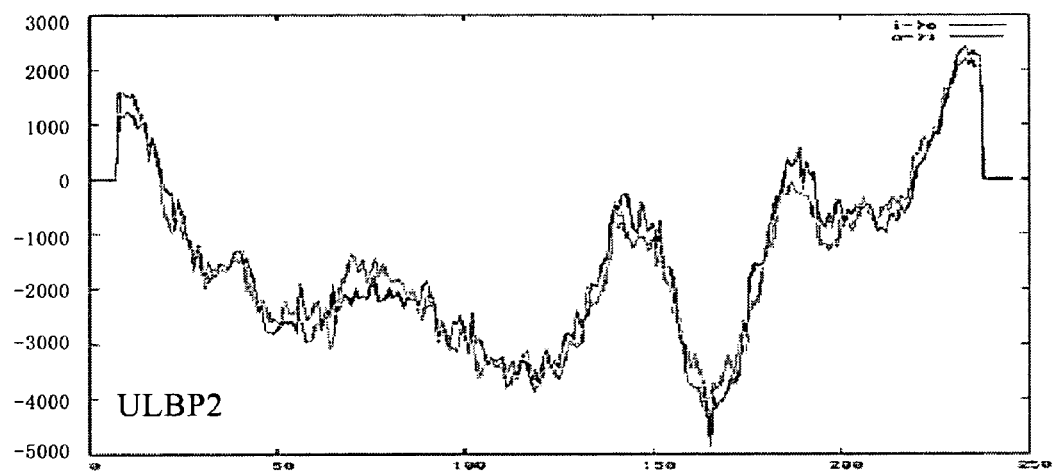

Analysis of the transmembrane structure of RL5 (FIG. 3) showed that the missing amino acid sequence in RL5 was the coding sequence of transmembrane region, indicating RL5 was a secreted antigen protein. Furthermore, the signal peptide analysis revealed that amino acids 1-28, encoded by nucleotides 1-84, was signal peptide.

As shown in FIGS. 2A and 2B, besides the C-terminus transmembrane region, the main difference between RL5 and ULBP2 was at the coding region of signal peptide at N-terminal. The extracellular regions of these two proteins were nearly the same.

EXAMPLE 3

Study on RL5 Expression

In Example 2, RL5 was predicted as a secreted protein according to software analysis. To confirm this prediction, RL5 cDNA was subcloned into a conventional eukaryotic expression vector pCDEF3-FLAG with a flag epitope at its carboxyl terminal, thereby forming pCDEF3-RL5-FLAG. 293T cells were transfected by pCDEF3-RL5-FLAG. Cells and supernatant of the cell culture were harvested after culturing for 24 hours. The cells were lysed. The anti-FLAG M2 antibody was used to immunoprecipitate the supernatant of cell culture. The anti-FLAG M2 antibody was used in the Western blotting for cell lysate, supernatant of cell culture, and the immunoprecipitates from the supernatant.

Figure 4:
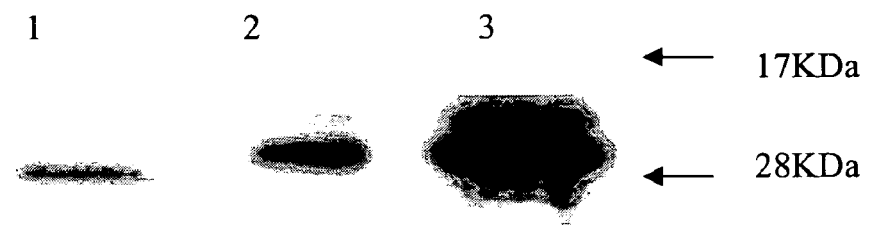
FIG. 4 shows the secretion expression of RL5. Lane 1 indicates the whole cell lysate of 293T-RL5, Lane 2 indicates the supernatant of 293T-RL5, and the Lane 3 indicates the immunoprecipitated products of the supernatant of 293T-RL5.

As shown in FIG. 4, most of the RL5-FLAG protein existed in the immunoprecipitates from the supernatant, indicating RL5 was a secreted protein indeed.

EXAMPLE 4

Recombinant Expression and Purification of RL5 Protein

In this example, the DNA sequence encoding human RL5 was amplified with the following oligonucleotide PCR primers corresponding to 5'- and 3'-end of RL5 DNA sequence using the PCR product obtained in Example 1 as the template. The resultant RL5 DNA was used as an insertion fragment.

The sequence of 5'-end oligonucleotide primer was:

```
                                          (SEQ ID NO:5)
5' ccggaattcGACCCTCACTCTCTTTGCTATGACA 3'
```

This primer contained a cleavage site of restriction endonuclease EcoRI, followed by the coding sequence of human RL5 without the signal peptide sequence.

The sequence of 3'-end primer was:

```
5' gccaagcttgatgccagggaggatgaagca 3' (SEQ ID NO:6)
```

This primer contained a cleavage site of restriction endonuclease HindIII, a stop codon and part of coding sequence of human RL5.

The PCR product of human RL5 cDNA was purified, digested with EcoRI/HindIII and linked into plasmid pProEXHTa (GIBCOBRL) according to the conventional method, thereby forming vector pProEXHTa-RL5. The vector pProEXHTa-RL5 was transformed into competent E. coli DH5α. The positive clones were identified, selected and sequenced (Model 377 sequencing machine from ABI company; BigDye Terminator kit from PE company). The sequencing results confirmed that the whole coding sequence of RL5 was inserted into the vector successfully.

The positive clone expressing RL5 was inoculated in 10 ml LB liquid medium and cultured in 37° C. overnight at 300 rpm, then added to fresh LB medium at 1:100 dilution and cultured for another 2.5 hr. 100 mM IPTG was added to final concentration of 0.1 mM and the bacteria were cultured for another 2-3 hr. Electrophoresis of the bacteria lysate after induction was run to determine the effect of IPTG-induction and results were shown in FIG. 5. Great difference in RL5 expression level was detected before and after induction, indicating the successful induction of RL5 expression.

RL5 was purified using the following procedure: The bacteria after induction were harvested by centrifugation at 5000 g for 10 minutes at 4° C. The supernatant was removed and pellet was resuspended with 50 ml loading buffer (0.5M NaCl, 20 mM imidozole, 2.7 mM KCl, 10.1 mM $Na_2HPO_4$, 1.8 mM $KH_2PO_4$, pH 8.0) on ice. The bacteria were sonicated so as to break the cells (B. Braun Labsonic U). The lysate was centrifuged at 12,000 g for 10 minutes at 4° C. After filtrated with 0.8-micrometer membrane filter, the supernatant was flowed through 1 ml $Ni^{2+}$ metal chelating Sepharose 4B chromatography column. After sufficiently washing with loading buffer, the column was eluted with 500 ul imidozole elution buffer (0.5M NaCl, 500 mM imidozole, 2.7 mM KCl, 10.1 mM $Na_2HPO_4$, 1.8 mM $KH_2PO_4$, pH 8.0). After standing at room temperature for 30 minutes, eluate was collected. The elution procedure was repeated for 2-3 times and RL5 protein was obtained (FIG. 6).

EXAMPLE 5

Tissue Expression Spectrum of RL5

Expression pattern of RL5 in tumor tissues and normal tissues was determined by RT-PCR, using the following internal primers in RL5 encoding region.

```
                                          (SEQ ID NO:7)
Forward primer:    5' ATGGCAGCGGCCGCCAGCCCC 3'

(SEQ ID NO:8)
Reverse primer:    5' TCAGATGCCAGGGAGGATGAAGCA 3'
```

The results were shown in FIG. 7. The housekeeping gene GAPDH was used as the positive control. A positive band was found in many kinds of tumor tissues, while no amplified fragment was found in the normal tissues, or the amplified fragments in normal tissues were significantly weaker than those in tumor tissues. These results showed that RL5 gene was expressed in tumor tissues such as stomach tumor, colon tumor, breast tumor, kidney tumor, and so on while it was not expressed or low expressed in normal tissues.

EXAMPLE 6

Discovery of Two Subtypes of RL5

The expression of RL5 was analyzed in Example 5. An interesting result was seen from FIG. 7, i.e., that all positive fragments formed two bands. These two bands were purified, cloned and sequenced. The results showed the sequence of small fragment was identical to that of RL5 cloned in Example 1, and there were 100 more bases in the sequence of large fragment. The large fragment was considered to be another subtype of RL5. The sequence was shown in SEQ ID NO: 9.

EXAMPLE 7

Quantitative PCR Analysis of RL5

To further confirm the expression of RL5 in various tumor tissues, 9 pairs of intestine tumor tissues and their corresponding normal tissues were selected and numbered 1N, 1T; 2N, 2T; ... 9N, 9T, wherein N represented normal tissues and T represented tumor tissues. RT-PCR and real-time fluorescent quantitative PCRs were used to study the qualitative and quantitative expression of RL5 in intestine tumor tissues.

| Tissue | Intestine tissue sample | Folds of change in RL5 expression (tumor vs. normal) |
|---|---|---|
| rectum | 1N-1T | 3.43 |
| rectum | 2N-2T | 8.49 |
| right semicolon | 3N-3T | 3.43 |
| ascending colon | 4N-4T | 2.48 |
| rectum | 5N-5T | 5.34 |
| sigmoid colon | 6N-6T | 18.57 |
| sigmoid colon | 7N-7T | 44.18 |
| colon | 8N-8T | 2.48 |
| terminal ileum | 9N-9T | 5.91 |

Figure 8A:
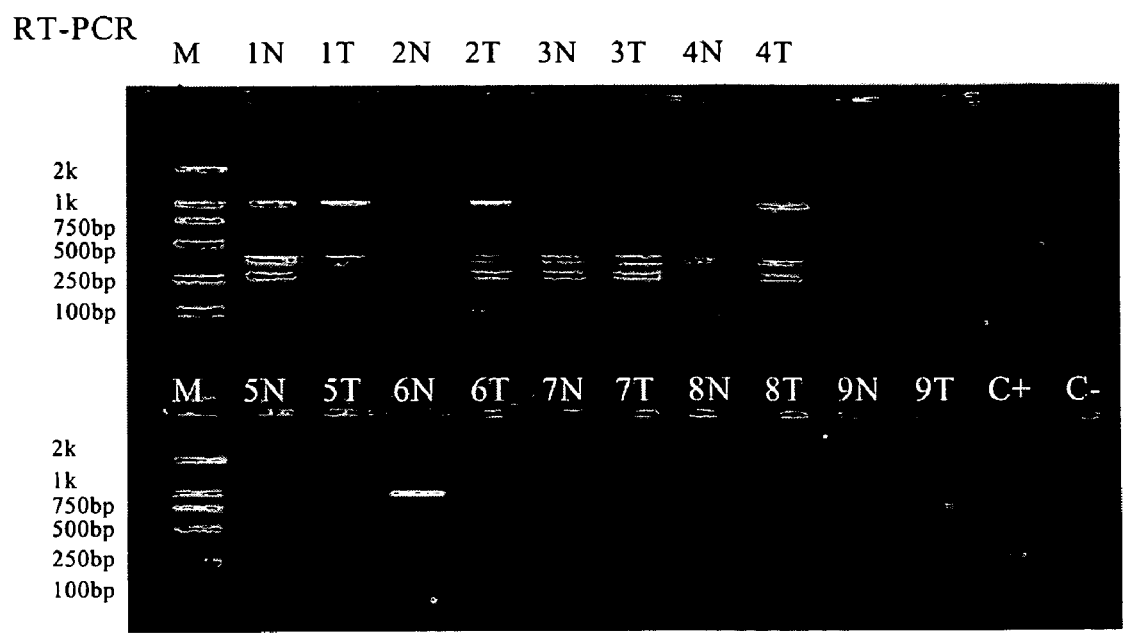
FIG. 8 shows the RT-PCR and quantitative PCR results of RL5 in 9 pairs of intestine tumor tissue samples.

The RT-PCR results in FIG. 8A showed that, the expression of RL5 was increased in some tumor tissues compared to the corresponding normal tissues, whereas in other samples, it had low expression or no expression.

Figure 8B:
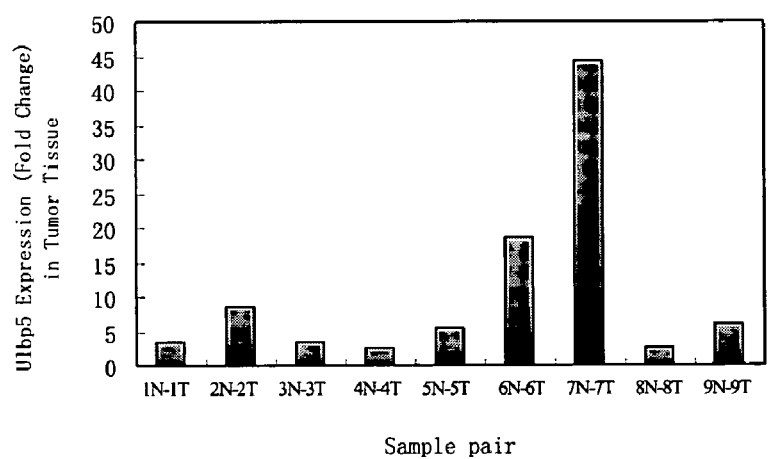

The results of quantitative PCR in FIG. 8B showed that, in all nine tumor tissues, the expression of RL5 was increased compared to the corresponding normal tissues. The maximum difference was 44 folds of the expression in normal tissue.

EXAMPLE 8

Interaction between RL-5 and NKG2D

The mice Ba/F3 cell line was transfected with a retrovirus vector containing NKG2D gene so that NKG2D receptor was expressed on the cell surface. 293T cell line was transfected with pCDEF3-RL5 and control plasmid pCDEF3. The cell supernatant was harvested after 24 hours. Since RL5 was a secretory protein, the supernatant containing RL5 protein and the control supernatant containing no RL5 protein were obtained. NKG2D-infected Ba/F3 cells were incubated with cell superannuate with RL5 (pCDEF3-RL5) or without RL5 (control plasmid pCDEF3) for 1 hour at room temperature, washed with PBS for three times, resuspended in 100 ul PBS, labeled as indicated hereinafter. The immunoflurescent signals were analyzed by FACS.

| | cell | First Antibody | Secondary antibody |
|---|---|---|---|
| A | Ba/F3-NKG-2D | Control antibody | Goat-anti-mIgG-FITC |
| B | Ba/F3-NKG-2D | Anti-NKG2D | Goat-anti-mIgG-FITC |

-continued

| | cell | First Antibody | Secondary antibody |
|---|---|---|---|
| C | Ba/F3-NKG-2D + RL5-supernatant (resuspended) | Anti-NKG2D | Goat-anti-mIgG-FITC |
| D | Ba/F3-NKG-2D + control supernatant (resuspended) | Anti-NKG2D | Goat-anti-mIgG-FITC |

Figure 9:
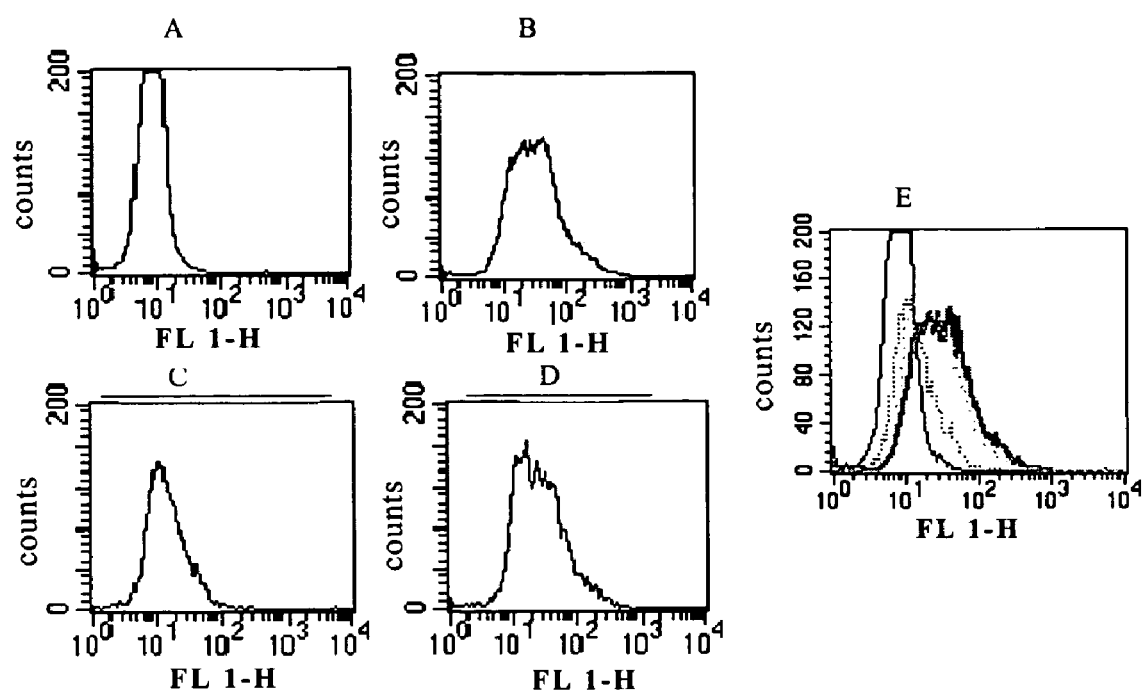
FIG. 9 shows the specific interactions between RL5 and NKG2D.

As shown in FIG. 9, there was no binding between NKG2D and control antibody (A). However, Ba/F3-NKG2D bound with NKG2D antibody (B), indicating NKG2D receptor was expressed on the cell surface of Ba/F3. No signal was detected from NKG2D-infected Ba/F3 cell, which incubated with cell supernatant containing RL5 and labeled with NKG2D antibody (C). However, in the control experiment, NKG2D-infected Ba/F3 cells were incubated with control cell supernatant without RL5 and labeled with NKG2D antibody. The results showed that NKG2D bound to the antibody (D). FIG. 9E was the overlay of FIGS. 9A-D. The results indicated RL5 was the ligand of NKG2D. RL5 bound with NKG2D receptor expressed on Ba/F3 cell surface and blocked the interaction between NKG2D and its antibody. In the control experiment, there was no RL5 protein and, therefore, the binding between NKG2D and the corresponding antibody was not blocked.

EXAMPLE 9

Preparation of Antibody Against RL5

Antibodies were produced by immunizing animals with the recombinant proteins obtained in Example 4. The method was as follows: the recombinant proteins were isolated by chromatography, and stored for use. Alternatively, the protein was isolated by SDS-PAGE electrophoresis, and obtained by cutting electrophoretic bands from gel. The protein was emulsified with Freund's complete adjuvant of the same volume. The emulsified protein was injected intraperitoneally into mice at a dosage of 50-100 ug/0.2 ml. 14 days later, the same antigen was emulsified with Freund's incomplete adjuvant and injected intraperitoneally into mice at a dosage of 50-100 ug/0.2 ml for booster immunization. Booster immunization was carried out every 14 days, for at least three times. The specific activity of the obtained antiserum was evaluated by its ability of precipitating the translation product of RL5 gene in vitro. The results confirmed that the specific binding between the antibody and the RL5 protein of the invention.

All the documents cited herein are incorporated into the invention as reference, as if each of them is individually incorporated. Further, it would be appreciated that, in the above teaching of invention, the skilled in the art could make certain changes or modifications to the invention, and these equivalents would still be within the scope of the invention defined by the appended claims of the application.

What is claimed is:

1. An isolated human RL5 polypeptide comprising the amino acid sequence of SEQ ID No: 2, or the amino acid sequence of 29-213 of SEQ ID NO:2.

2. The polypeptide of claim 1 wherein the polypeptide consists of the amino acid sequence of 1-213 of SEQ ID NO: 2 or the amino acid sequence of 29-213 of SEQ ID NO: 2.

3. An isolated polynucleotide which is selected from the group consisting of:

(a) a nucleotide sequence encoding the polypeptide comprising the amino acid sequence of SEQ ID NO: 2; and (b) a nucleotide sequence encoding a polypeptide comprising the amino acid sequence of 29-213 of SEQ ID NO: 2.

4. The isolated polynucleotide of claim 3 which encodes a polypeptide comprising the amino acid sequence of 29-213 of SEQ ID NO: 2.

5. The isolated polynucleotide of claim 3 which is selected from the group consisting of (a) the nucleotide sequence of 85-639 of SEQ ID NO: 1;
(b) the nucleotide sequence of 1-639 of SEQ ID NO: 1; and
(c) the nucleotide sequence of 1-720 of SEQ ID NO: 1.

6. A vector containing the isolated polynucleotide of claim 3.

7. An isolated genetically engineered host cell comprising the vector of claim 6.

8. A method for producing RL5, protein which comprises:

(a) culturing an isolated genetically engineered host cell comprising the vector of claim 6, thereby expressing RL5 protein in a culture of the host cells; and (b) isolating RL5 protein from the culture of step (a).

9. An isolated human RL5 polypeptide wherein the polypeptide is encoded by the isolated polynucleotide of claim 3.

10. The polypeptide of claim 9 wherein the polypeptide is encoded by the polynucleotide selected from the group consisting of:

(a) the nucleotide sequence of 85-639 of SEQ ID NO: 1;
(b) the nucleotide sequence of 1-639 of SEQ ID NO: 1; and
(c) the nucleotide sequence of 1-720 of SEQ ID NO: 1.

* * * * *

SEQUENCE LISTING

<160> NUMBER OF SEQ ID NOS: 9

<210> SEQ ID NO 1
<211> LENGTH: 48
<212> TYPE: DNA
<213> ORGANISM: Artificial
<220> FEATURE:
<223> OTHER INFORMATION: oligonucleotide

<400> SEQUENCE: 1
atggcagcgg ccgccagccc cgcgttcctt ctacgcctcc cgcttctg                    48

<210> SEQ ID NO 2
<211> LENGTH: 213
<212> TYPE: PRT
<213> ORGANISM: Homo sapiens

<400> SEQUENCE: 2

Met Ala Ala Ala Ala Ser Pro Ala Phe Leu Leu Arg Leu Pro Leu Leu
1               5                   10                  15

Leu Leu Leu Ser Ser Trp Cys Arg Thr Gly Leu Ala Asp Pro His Ser
            20                  25                  30

Leu Cys Tyr Asp Ile Thr Val Ile Pro Lys Phe Arg Pro Gly Pro Arg
        35                  40                  45

Trp Cys Ala Val Gln Gly Gln Val Asp Glu Lys Thr Phe Leu His Tyr
    50                  55                  60

Asp Cys Gly Ser Lys Thr Val Thr Pro Val Ser Pro Leu Gly Lys Lys
65                  70                  75                  80

Leu Asn Val Thr Thr Ala Trp Lys Ala Gln Asn Pro Val Leu Arg Glu
                85                  90                  95

Val Val Asp Ile Leu Thr Glu Gln Leu Leu Asp Ile Gln Leu Glu Asn
            100                 105                 110

Tyr Ile Pro Lys Glu Pro Leu Thr Leu Gln Ala Arg Met Ser Cys Glu
        115                 120                 125

Gln Lys Ala Glu Gly His Gly Ser Gly Ser Trp Gln Leu Ser Phe Asp
    130                 135                 140

Gly Gln Ile Phe Leu Leu Phe Asp Ser Glu Asn Arg Met Trp Thr Thr
145                 150                 155                 160

Val His Pro Gly Ala Arg Lys Met Lys Glu Lys Trp Glu Asn Asp Lys
                165                 170                 175

Asp Met Thr Met Ser Phe His Tyr Ile Ser Met Gly Asp Cys Thr Gly
            180                 185                 190

Trp Leu Glu Asp Phe Leu Met Gly Met Asp Ser Thr Leu Glu Pro Ser
        195                 200                 205

Ala Gly Gly Thr Val
    210

<210> SEQ ID NO 3
<211> LENGTH: 29
<212> TYPE: DNA
<213> ORGANISM: Artificial
<220> FEATURE:
<223> OTHER INFORMATION: oligonucleotide

<400> SEQUENCE: 3
cggaattcat ggcagcggcc gccagcccc                                         29

<210> SEQ ID NO 4
<211> LENGTH: 30
<212> TYPE: DNA
<213> ORGANISM: Artificial
<220> FEATURE:
<223> OTHER INFORMATION: oligonucleotide

<400> SEQUENCE: 4
gccaagcttg atgccaggga ggatgaagca                                       30

<210> SEQ ID NO 5
<211> LENGTH: 34
<212> TYPE: DNA
<213> ORGANISM: Artificial
<220> FEATURE:
<223> OTHER INFORMATION: oligonucleotide

<400> SEQUENCE: 5
ccggaattcg accctcactc tctttgctat gaca                                  34

<210> SEQ ID NO 6
<211> LENGTH: 30
<212> TYPE: DNA
<213> ORGANISM: Artificial
<220> FEATURE:
<223> OTHER INFORMATION: oligonucleotide

<400> SEQUENCE: 6
gccaagcttg atgccaggga ggatgaagca                                       30

<210> SEQ ID NO 7
<211> LENGTH: 21
<212> TYPE: DNA
<213> ORGANISM: Artificial
<220> FEATURE:
<223> OTHER INFORMATION: oligonucleotide

<400> SEQUENCE: 7
atggcagcgg ccgccagccc c                                                21

<210> SEQ ID NO 8
<211> LENGTH: 24
<212> TYPE: DNA
<213> ORGANISM: Artificial
<220> FEATURE:
<223> OTHER INFORMATION: oligonucleotide

<400> SEQUENCE: 8
tcagatgcca gggaggatga agca                                             24

<210> SEQ ID NO 9
<211> LENGTH: 60
<212> TYPE: DNA
<213> ORGANISM: Artificial
<220> FEATURE:
<223> OTHER INFORMATION: oligonucleotide

<400> SEQUENCE: 9
atggcagcgg ccgccagccc cgcgttcctt ctacgcctcc cgcttctgct cctgctgtcc      60